(12) United States Patent
Schalliol

(10) Patent No.: US 8,177,843 B2
(45) Date of Patent: May 15, 2012

(54) AUTOMATED PEDICLE SCREW ROD BENDER

(75) Inventor: David L. Schalliol, Oakwood, GA (US)

(73) Assignee: Nabil L. Muhanna, Gainesville, GA (US)

( * ) Notice: Subject to any disclaimer, the term of this patent is extended or adjusted under 35 U.S.C. 154(b) by 1771 days.

(21) Appl. No.: 11/355,593

(22) Filed: Feb. 16, 2006

(65) Prior Publication Data
US 2007/0227216 A1 Oct. 4, 2007

(51) Int. Cl.
*A61F 2/44* (2006.01)
*A61B 17/70* (2006.01)
*B21D 7/14* (2006.01)
(52) U.S. Cl. ............... 623/17.11; 606/246; 72/31.05
(58) Field of Classification Search .......... 606/246–278; 72/31.04–31.05; 623/17.11–17.16
See application file for complete search history.

(56) References Cited

U.S. PATENT DOCUMENTS

| 5,818,958 A | 10/1998 | Tomiyama et al. |
| 6,035,691 A * | 3/2000 | Lin et al. .................. 72/413 |
| 6,616,444 B2 | 9/2003 | Andreiko et al. |
| 2005/0262911 A1 * | 12/2005 | Dankowicz et al. ......... 72/31.04 |

OTHER PUBLICATIONS

Langholts et al. A Pilot Study on Computer-Assisted Optimal Contouring of Orthopedic Fixation Device, Sep. 24, 1999, Computer Aided Surgery, 4:305-315.*

* cited by examiner

*Primary Examiner* — Thomas C. Barrett
*Assistant Examiner* — Matthew Lawson
(74) *Attorney, Agent, or Firm* — Womble Carlyle Sandridge & Rice, LLP

(57) ABSTRACT

An automated screw rod bender includes a sensing system for sensing a position of each of a plurality of screws that are inserted into a vertebrae, a computing system for converting the positions into a geometric coordinates of the screws and generating a corresponding plurality of rod bending parameters, and a rod bending system for bending a rod based on the rod bending parameters.

6 Claims, 13 Drawing Sheets

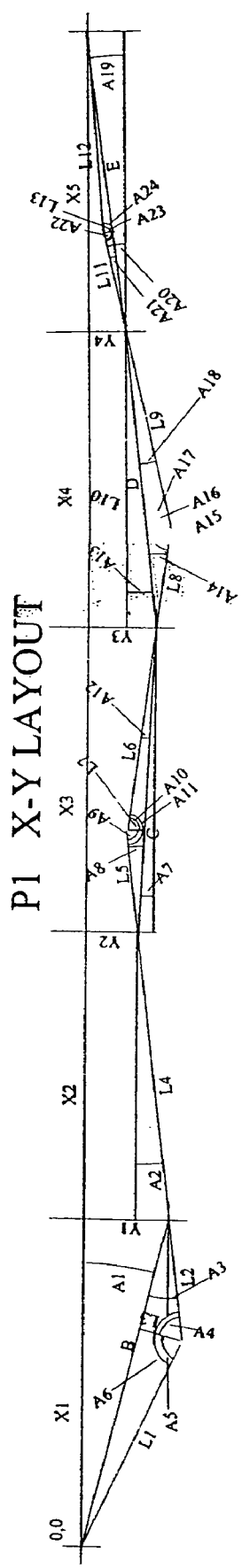

P1 X-Y LAYOUT

FIG 7

A1=1/TAN (Y1/X1)
A2=1/TAN ((Y1-Y2)/(X2-X1))
A3=A1+A2
B=X1 / COS A1
A4= 90-A3
L2= (B/3) / COS A3
L3= L2 * SIN A3
A5=1/TAN ((2B/3)/L3)
L1= (2B/3) / SIN A5
A6= A4 + A5
BEND #1 = 180 - A6

L4 =(X2-X1) / COS A2
A7 =1/TAN ((Y3-Y2)/(X3-X2))
A8= A7 + A2
C= (X3-X2) / COS A7
L5= (C/3) / COS A8
L7= L5 * SIN A8
A9= 90-A8
A10= 1/TAN ((2C/3)/L7)
L6= (2C/3) / SIN A10
A11= A9 + A10
A12= 90-A10
BEND #2 = 180 - A11

A13 =1/TAN ((Y3-Y4)/(X4-X3))
D= (X4-X3) / COS A13
A14= A7 + A12 + A13
A15= 90 - A14
L10= L8 * SIN A14
A16= 1/TAN ((2D/3)/L10)
L8= (D/3) / COS A14
A17= A15 + A16
L9= (2D/3) / SIN A16
A18= 90 - A16
BEND #3 = 180 - A17

A19 =1/TAN (Y4/(X5-X4))
A20 = A18 + A13
A21 = A20 - A19
E= (X5-X4) / COS A19
L11= (E/3) / COS A20
L13= L11 * SIN A21
A22= 90 - A21
A23= 1/TAN ((2E/3)/L13)
A24= A22 + A23
L12= (2E/3) / SIN A23
BEND #4 = 180 - A24

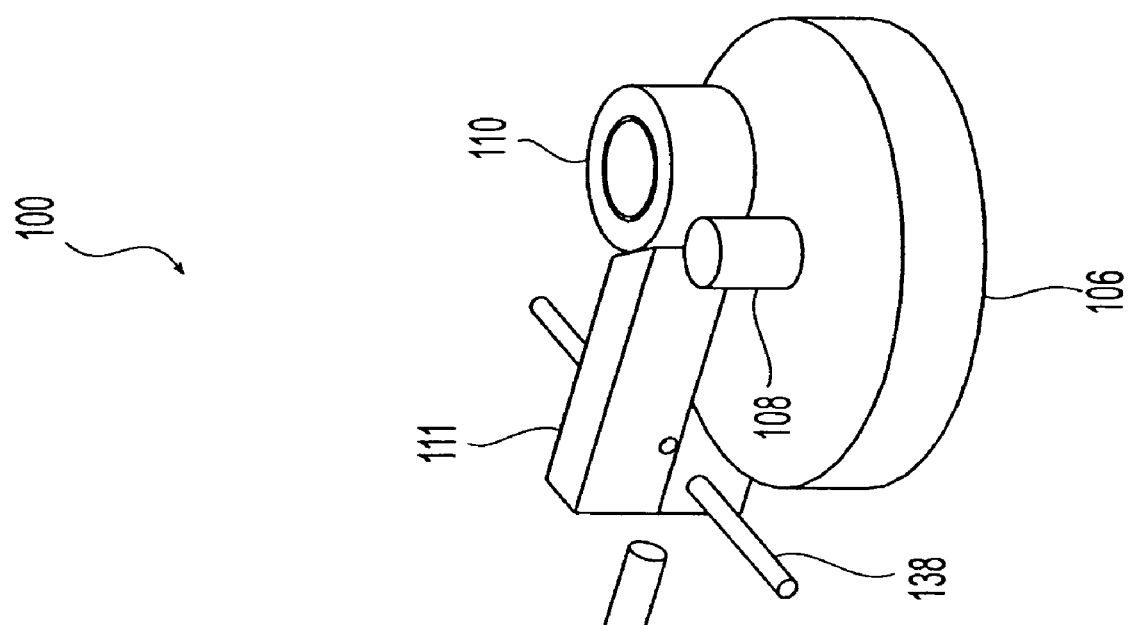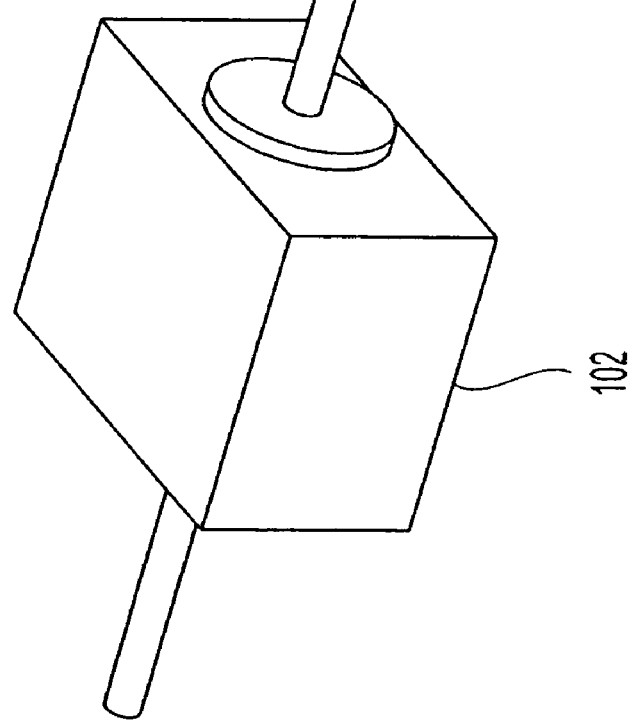
Fig. 11

AUTOMATED PEDICLE SCREW ROD BENDER

FIELD OF THE INVENTION

One embodiment of the present invention is directed to a medical device. More particularly, one embodiment of the present invention is directed to an automated pedicle screw rod bender.

BACKGROUND INFORMATION

Bone screws have been used in spinal instrumentation since the 1960s. A pedicle screw is a particular type of bone screw designed for implantation into a vertebral pedicle. The pedicle is a dense stem-like structure that projects from the posterior of a vertebra. There are two pedicles per vertebra that connect to other structures (e.g., lamina, vertebral arch).

During back surgery, particularly in the lumbar area, pedicle screws and rods must be inserted into the vertebrae to provide mechanical support to the spine during the healing and bone fusion process. Typically the pedicle screws are inserted as close as possible to a straight line, to minimize the bends required in the rods that connect them. It is quite difficult to get the connecting rod axis straight, due to the geometry of the spinal bodies, and the inherent curvature of even a healthy spine.

To achieve a fit of a single rod passing through these multiple screws, the surgeon typically will bend a template rod of soft material (e.g., tin), and then attempt to duplicate this rod from much stiffer alloys such as titanium. This duplication process requires much trial and error, and is a difficult, time consuming, and frustrating experience. The longer the rod, the more bends are required, and the more difficult the process.

Based on the foregoing, there is a need for a system and method for automatically forming a pedicle screw rod.

SUMMARY OF THE INVENTION

One embodiment of the present invention is an automated screw rod bender that includes a sensing system for sensing a position of each of a plurality of screws that are inserted into a vertebrae, a computing system for converting the positions into a geometric coordinates of the screws and generating a corresponding plurality of rod bending parameters, and a rod bending system for bending a rod based on the rod bending parameters.

BRIEF DESCRIPTION OF THE DRAWINGS

FIGS. 7 and 8 graphically illustrate a typical calculation sheet for a five level procedure.

FIG. 11 is an additional perspective view of the bending system in accordance with one embodiment of the present invention.

DETAILED DESCRIPTION

One embodiment of the present invention is a pedicle screw rod bender system that includes a sensing system for determining the coordinates of the pedicle screws, a computer interface system for calculating the shape of the rod based on the coordinates, and a bending system for automatically bending a rod into the predetermined shape.

Figure 1:
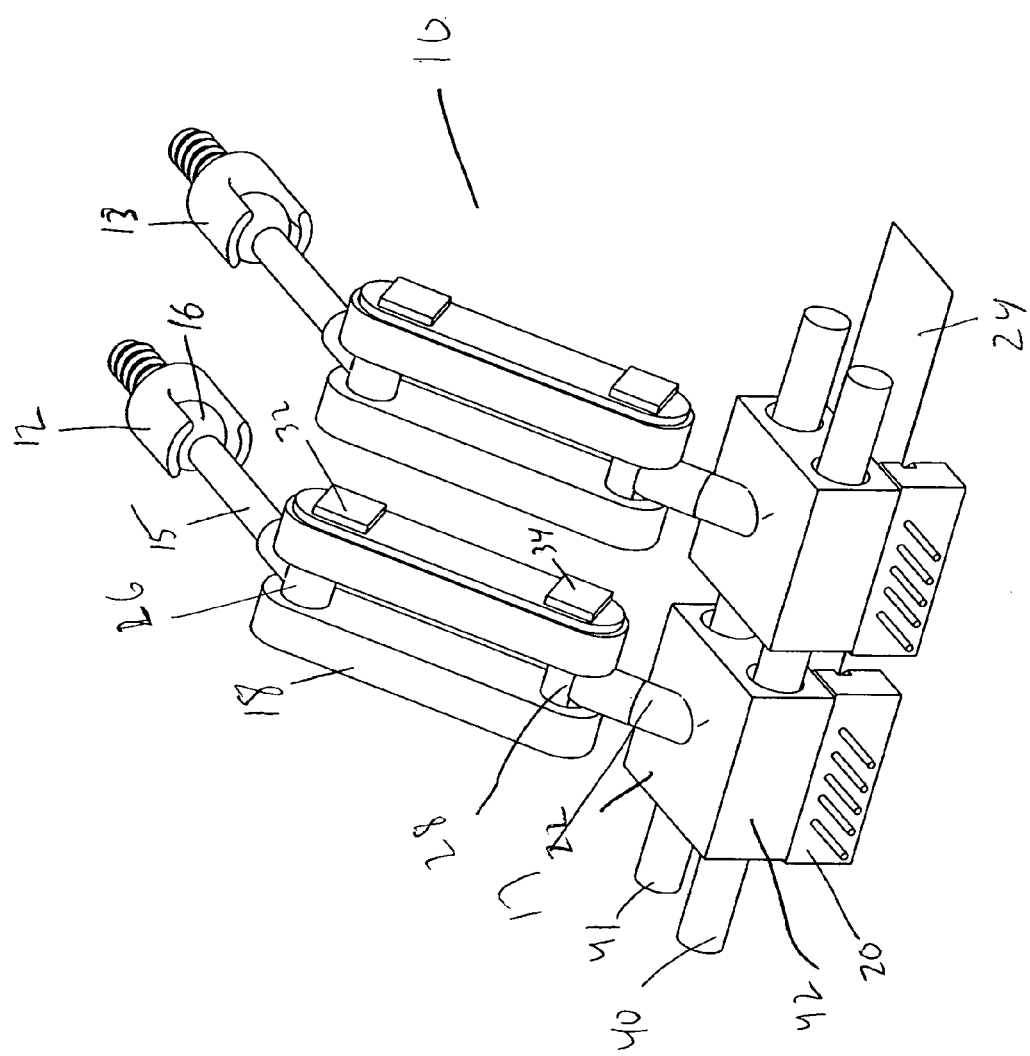
FIG. 1 is a perspective view of a sensing system in accordance to one embodiment of the present invention for sensing the coordinates of pedicle screws.

FIG. 1 is a perspective view of a sensing system 10 in accordance to one embodiment of the present invention for sensing the coordinates of pedicle screws 12 and 13. Sensing system 10 uses linear and rotary encoders to determine the X, Y, & Z coordinates of each screw. Sensing system 10 is a hand held coordinate measurement device that is taken directly to the patient. Through the use of conforming measurement balls and linkages, the three dimensional position of each screw is determined.

For each screw to be sensed, sensing system 10 includes a sensing arm. Each sensing arm includes a sensor measurement ball 16. Measurement ball 16 is pressed into the screw's internal spherical conforming socket by finger pressure. The surgeon can apply and feel the pressure required to seat the balls in each screw socket. Additional pressure can be applied to actually move or form the spine to a more desired axis. When the feel and fit are correct, a single push button or keystroke will cause a position capture.

Each sensor arm further includes a pair of joint hinge pins 26 and 28, shafts 15 and 17, and bracket 18. A pair of rotary sensors 32 and 34 sense the coordinates of shafts 15 and 17. In one embodiment, the rotary sensors are part numbers AS5045 from austriamicrosystems. Shaft 17 is coupled to a sensor slide block 42 that is mounted on a pair of linear shafts 40 and 41. Slide block 42 includes an encoder chip. In one embodiment, the encoder chip is linear encoder part number EM1-0-250 from US Digital Corporation. A linear sensor within block 42 measures the position of block 42 on linear shafts 40 and 41. The position and coordinate data (i.e., the X, Y, & Z coordinates of each screw) is transmitted from each arm on a linear optical encoder strip 24. In one embodiment, the encoder strip is part number LIN-250 from US Digital Corporation.

Sensing system 10 fits comfortably in the surgeon's hands, and as many as eight screws can be sensed using the surgeon's eight available fingers. When more than eight screws are needed to be sensed, more than one set of surgeon's hands can be incorporated.

Rotary sensors 32 and 34 on hinge pins 26 and 28 in one embodiment each include a small flat precision magnetic disk, which generates a field that penetrates the Hall Effect Elements in the end mounted encoder chip. The encoder chip includes a Digital Signal Processing ("DSP") processor, which can resolve the rotation of the hinge pin into 4096 incremental steps per revolution using either quadrature encoding output or an absolute position serial output stream. The serial data is sent to a computer via an RS232 port, where it is directed and inserted into predetermined cells of a spreadsheet. In one embodiment, the spreadsheet is the Excel spreadsheet from Microsoft Corp.

In one embodiment in which a quadrature output is used, a counter and microcontroller is included to convert the quad four code to a serial stream as above. The two hinge positions and the known lengths of the sensor arms are all that is needed to determine the Y & Z coordinates of each screw. Linear encoder strip 24 and its corresponding reader sensor also generates a quadrature signal with a 1000 count per inch resolution. This signal is also converted to a serial stream and is sent to the same spreadsheet. Data from this linear encoder forms the X coordinates of the screw.

Figure 2:
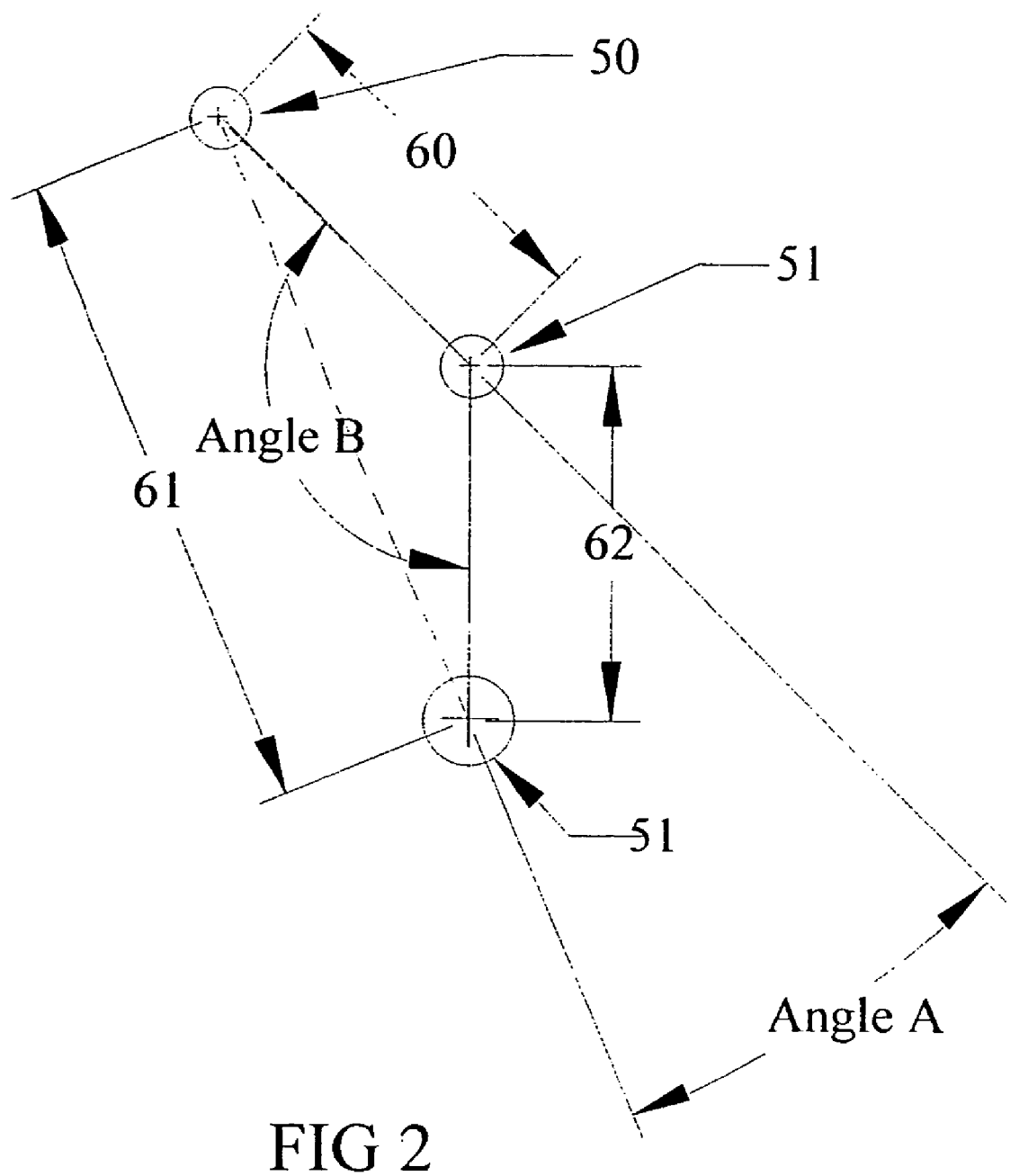
FIG. 2 is a graphical diagram illustrating the geometric layout of each sensor arm of a sensor system in accordance with one embodiment of the present invention.

FIG. 2 is a graphical diagram illustrating the geometric layout of each sensor arm of sensor system 10 in accordance with one embodiment of the present invention. Shown is FIG. 2 is top hinge pin 50, bottom hinge pin 51, and sensor measurement ball 52. In one embodiment, distance 60 between top hinge pin 50 and bottom hinge pin 51, and distance 62 between bottom hinge pin 51 and measurement ball 52 is 1.5", distance 61 between top hinge pin 50 and measurement ball 52 is 2.78", and the diameter of measurement ball 52 is 0.375". Further, Angle B is 135° and Angle A is 22.5°.

The graphical diagram of FIG. 2 shows the sensor arm in the "mastered" or "zero" position, i.e., the encoder counters for Angle A and Angle B would be set to zero. In the mastered position, the lower finger is vertical, and the upper finger is set at 45 degrees from vertical.

Figure 3:
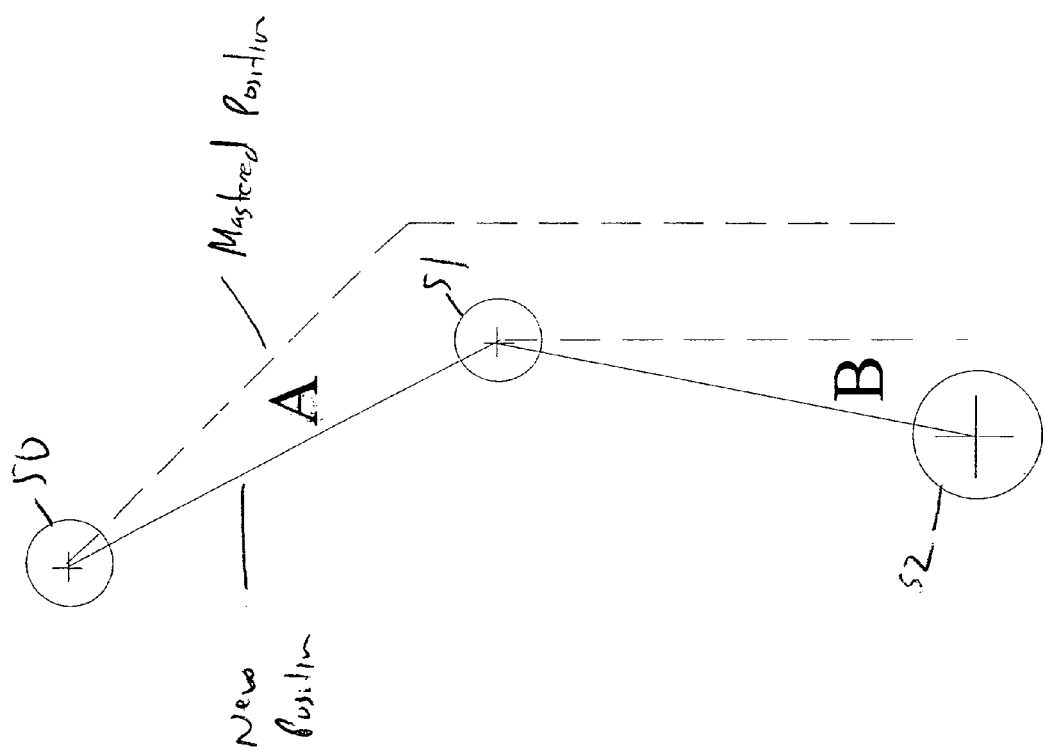
FIG. 3 is a graphical diagram illustrating the geometric layout of the sensor arm of FIG. 2 in which the sensor arm is deflected away from the mastered position.

FIG. 3 is a graphical diagram illustrating the geometric layout of the sensor arm of FIG. 2 in which the sensor arm is deflected away from the mastered position. In this case, the counters would both contain a non-zero number, and the new counter value would be sent serially to the spreadsheet at the capture command.

The actual new position values (relative to the mastered position) can be calculated by the spreadsheet using the following equations:

$$Y=(SIN(A)\times 2.78)+(SIN(A+B)\times 1.5)$$

$$Z=((COS(A)-COS(A+B)\times 1.5))-(((COS(22.5-A)-(COS\ 22.5))\times 2.78))$$

The above equations are disclosed to clarify how angular displacement can be used to calculate linear coordinates in one embodiment of the present invention. This conversion is only necessary for the Y & Z-axis. The X axis readings from the linear encoder is already in linear units in one embodiment.

Figure 4:
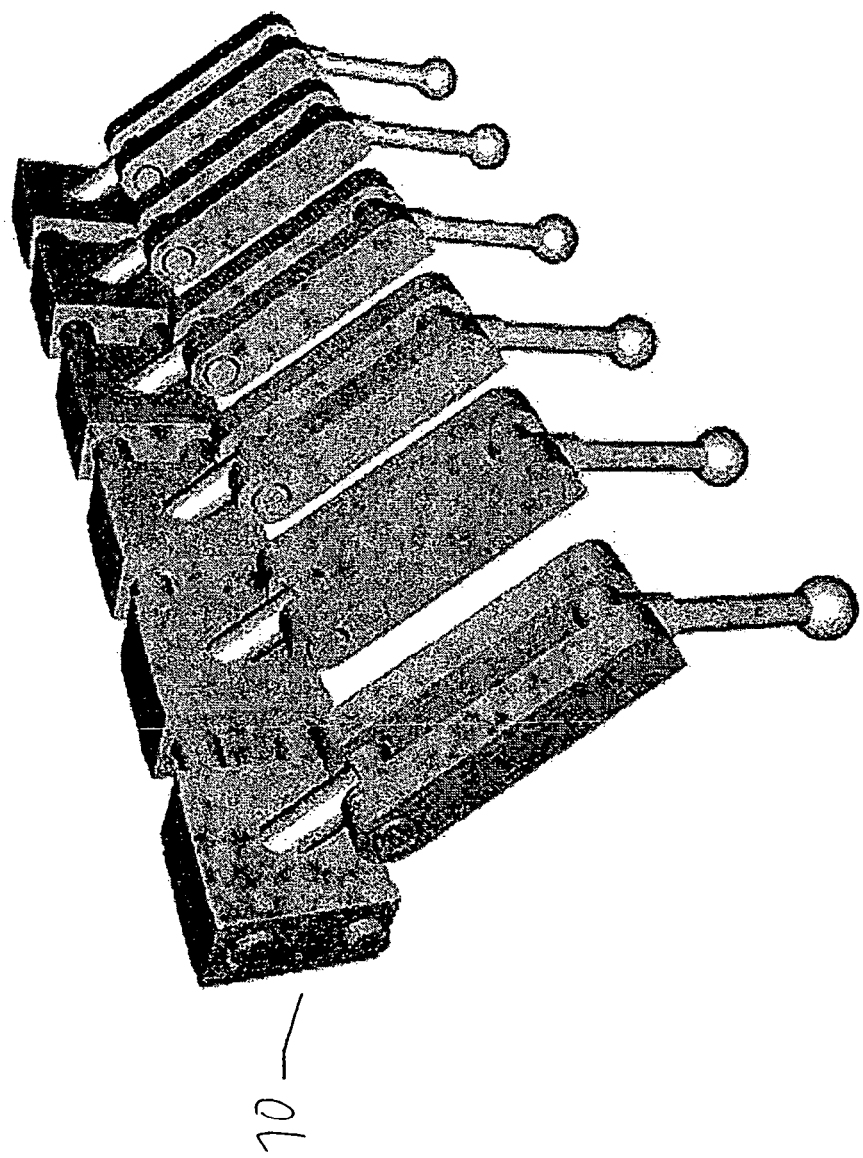
FIG. 4 is a perspective view of a sensor system that includes six sensor arms in the mastered position in accordance with one embodiment of the present invention.

FIG. 4 is a perspective view of a sensor system 70 that includes six sensor arms in the mastered position in accordance with one embodiment of the present invention. Note that the sensor arms on opposite ends are mechanically locked (not allowed to rotate), and the left most sensor (which is referred to as "sensor #1") is locked to the slide bars so that it cannot move axially. There are no encoders on this sensor, as it will always be at the origin (coordinates 0,0,0). The encoder on the right (sensor #6) in the mastered position will have coordinates of 6,0,0. The 6 refers to 6.000 inches, since each slide block is 1.000" wide, and all slide blocks are squeezed together during mastering.

The assumed logic for taking a measurement is that a straight line can be drawn through all sensor balls while they are in the mastered position. When the sensor balls are moved, a straight line can still be drawn through the balls at the opposite ends, since their Y & Z positions are locked. The length of the line connecting these outer ball centers will change as the balls are moved axially, but the linear encoder located on the back of sensor #6 records this motion. Motion of the intermediate sensors (between the two ends) will simply be the deviation from the above straight line for the Y & Z-axis, and the linear encoder deviation from mastered will reflect the X axis distance.

The sensor system shown above would be used in a five level surgery. "Level" refers to the number of discs involved in the procedure. The level # is always be one less than the number of screws. Further, any number of levels can be accomplished by simply adding or removing sensor arms from the system. Sensors arms need not actually be removed. Instead, they are disabled or not read by the software during the position scan. The only mechanical change required to the hardware would be locking the appropriate joints on the right most sensor arm used. For a four level surgery, the top and bottom hinge pin on sensor finger five would be locked from rotation. The sensor arms for positions five and six would merely hang in space and their encoders not read.

Figure 5:
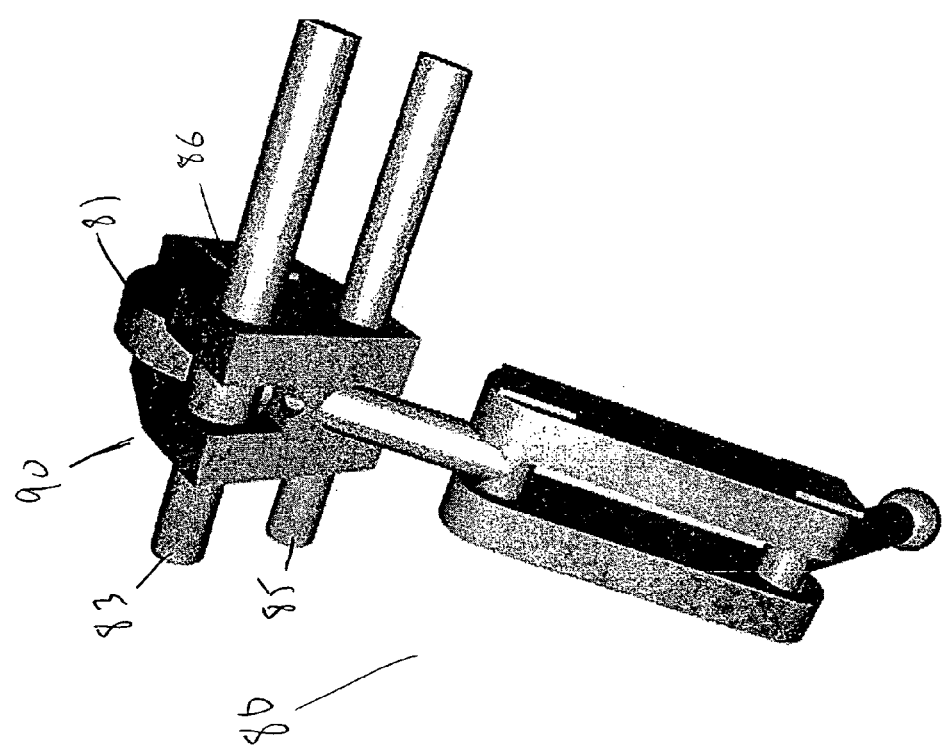
FIG. 5 is a perspective view of a sensor arm in accordance with another embodiment of the present invention.

FIG. 5 is a perspective view of a sensor arm 70 in accordance with another embodiment of the present invention. The lower half is the same as the sensor arms of FIG. 1. However, sensor block 90 is changed significantly. Sensor block 90 is narrower (0.75" wide), it uses an offset geared thumb-wheel 81 with the same rotary magnetic sensor 86 as used in the lower half, and top horizontal shaft 83 is now threaded. Top shaft 83 is still stationary and is still the same diameter as the bottom horizontal shaft 85. Top shaft 83 has 20 threads/inch, and has a small floating threaded bore gear that is trapped axially by the block body. As this small gear is rotated, it forces the complete sensor assembly to move axially. This small gear has a pitch diameter of 0.333/0.335". This small gear is meshed with a larger gear with a pitch diameter of 1.00", or a ratio of 3:1. This large gear, shown to the rear of the small gear, is fixed to a small stub shaft. The stub shaft provides bearing support (plastic bushings), and a mounting surface for the magnet which rotates under the magnetic rotary encoder.

Large gear 81 serves a thumb-wheel or knob that the surgeon can easily move, even with rubber gloves. One full rotation of the thumb-wheel will cause three rotations of the small gear. Since the threaded rod has 20 threads/inch (0.050" pitch), one revolution of the thumb-wheel actually moves the assembly 0.150" axially. The magnetic encoder has 4096 counts/rev, which equates to an axial resolution of 0.0000366"/count, which is far better than required for anticipated requirements.

As disclosed, the sensor system is coupled to a computer system to calculate the coordinates. Although the rotary and linear sensors used in the sensor system are different technology and typically not used together in a common system, they do have an output configuration in common, and that is the two line quadrature signal. The quadrature signal from either type sensor is fed into a four-channel (four-sensor) converter. In one embodiment, the converter is model no. AD5 from US Digital Corporation. Within this converter are 4 up/down counters that monitor the sensor status (counts) in real time. Also contained within the converter is a microcontroller that can read any selected sensor/counter on demand and place the binary numerical data on a bi-directional serial communication bus (RS-485). Several of these four-channel converters (up to 15) can share a common serial bus. At the computer end of the bus is another converter that translates the (RS-485) serial information into the more common RS-232 standard, readable by any general purpose computer.

Figure 6:
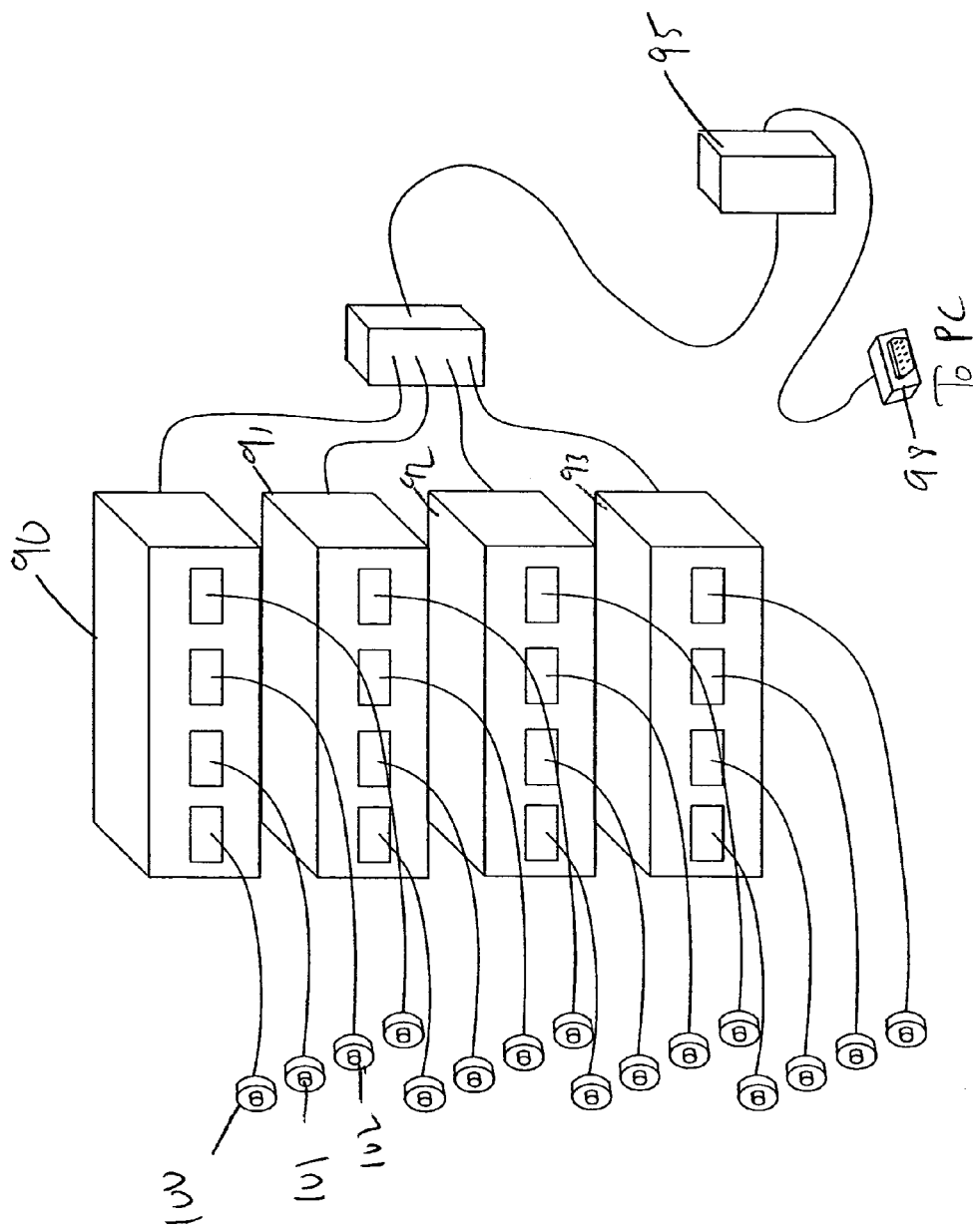
FIG. 6 is a perspective view illustrating an interface between the sensing system and the computer system in accordance with one embodiment of the present invention.

FIG. 6 is a perspective view illustrating an interface between the sensing system and the computer system in accordance with one embodiment of the present invention. Sixteen encoders 100, 101, 102 . . . , are coupled through quadrator to RS-485 converters 90-93. An RS-485 to RS-232 converter 95 couples the encoders to the computer through serial connector 98. In one embodiment, the RS-485 to RS-232 converter is part number AD2-B from US Digital Corporation. Sixteen encoders, as shown in FIG. 6 is suitable to read screw positions on a six level surgery. Further encoders and converters can be added to read a larger number of screw positions.

As disclosed above, the magnetic rotary encoders are also capable of placing their data directly on a RS-485 or equivalent serial bus, which would eliminate the need for the intermediate quad to RS-485 converters 90-93. However, due to the limitation of the linear encoders used in one embodiment, which lack this intelligence, the more hardware intensive approach in FIG. 6 is implemented. In other embodiments, as more intelligent linear optical encoders become available, this system can be simplified.

The quad to RS-485 converters are intelligent and need only a query to a particular address (encoder position) to return data. The requested address is actually generated in the spreadsheet, however there is a need to open a DDE (dynamic data exchange) channel through another software package to do so. There is also a need to convert the raw binary data to HEX (hexadecimal) characters before it can be accepted into a Macro in Excel. In one embodiment, WinWedge software handles the DDE communication and the conversion, as well as a Hot Key (data capture operator prompt) to start a sensor read and conversion. As the Hot Key is pressed on the keyboard, WinWedge starts a macro in Excel, which has three functions. The first is that it sends out the necessary prompts to the quad to RS-485 converters in sequence to read the encoders one at a time and prepare the appropriate Excel cell for the data. The second is that it does a Hex to Decimal conversion on the data. The third function is that it scales the data into the appropriate form (division, decimal points, etc.), and places it in the appropriate cell. The following is an example of the Excel macro, written in Visual basic, in accordance to one embodiment of the present invention:

```
Public Const MyPort = "COM2"         ' Change port to match configuration of WinWedge
Public Const MaxPrompts As Long = 13  ' define the number of prompts or devices
Dim RowPointer As Long                ' create variable to keep track of which row the data will be
    written to
Dim Prompt(MaxPrompts) As String      ' create a string array of prompts
Sub GetSWData( )
Dim x As Long
Dim ChannelNum As Long
Dim MyData As Variant
Dim MyDataString As String
' the variable PNum keeps track of which prompt was sent last - start with
device 1
Static PNum As Long          ' preserve the value of PNum between calls
If PNum = 0 Then
PNum = 1          ' Set the initial value of PNum to 1
RowPointer = Sheets("Sheet1").Cells(65000, 1).End(xlUp).Row + 1
End If
' define the specific prompts for each device - add a line for each prompt
' see the Wedge manual for details about the SENDOUT command
' WinWedge will send the first prompt so we do not need to define it here
Prompt(2) = "[SENDOUT(33)]"       ' prompt for device 2
Prompt(3) = "[SENDOUT(49)]"       ' prompt for device 3
Prompt(4) = "[SENDOUT(65)]"       ' prompt for device 4
Prompt(5) = "[SENDOUT(18)]"       ' prompt for device 5
Prompt(6) = "[SENDOUT(16)]"       ' prompt for device 6
Prompt(7) = "[SENDOUT(32)]"       ' prompt for device 7
Prompt(8) = "[SENDOUT(48)]"       ' prompt for device 8
Prompt(9) = "[SENDOUT(64)]"       ' prompt for device 9
Prompt(10) = "[SENDOUT(34)]"      ' prompt for device 10
Prompt(11) = "[SENDOUT(50)]"      ' prompt for device 11
Prompt(12) = "[SENDOUT(66)]"      ' prompt for device 12
Prompt(13) = "[SENDOUT(19)]"      ' prompt for device 13
If RowPointer = 0 Then RowPointer = 2           ' start saving data in row 2
On Error Resume Next               ' ignore errors
ChannelNum = DDEInitiate("WinWedge", MyPort)    ' open a DDE link to WinWedge
MyData = DDERequest(ChannelNum, "FIELD(2)")     ' get data from field(2)
' the above line gets the response from the last prompt that was sent
MyDataString = MyData(1) ' convert variant array type to a string variable
' The data from Field(1) of WinWedge is now in the variable "MyDataString"
Sheets("Sheet1").Cells(RowPointer, PNum).Formula = Val("&" & MyDataString)
' the above line writes the data to column "PNum" in row "RowPointer"
' PNum indicates which prompt requested the data that we just got
PNum = PNum + 1          ' Increment Prompt Number - count from 1 to MaxPrompts%
If PNum > MaxPrompts Then       ' If PNum>MaxPrompts% then set it back to 1
PNum = 1          ' Wedge will send the prompt for first device
RowPointer = RowPointer + 1          ' increment RowPointer so that the next batch of data gets
written to the next row down
Else                     ' otherwise send the prompt for the next device
  DDEExecute ChannelNum, Prompt(PNum)     ' send the next prompt
End If
```

```
DDETerminate ChannelNum          ' terminate the link
End Sub
```

At the press of a single key, the conditioned encoder data will appear in a horizontal row starting in row two of the Excel spreadsheet. Data from rotary encoders will first have to be converted to angles, and then through the use of trigonometry and known lever arms, to Y & Z coordinates. The trigonometry equations to do these conversions are as follows:

$$Y = (SIN(A) \times 2.78) + (SIN(A+B) \times 1.5)$$

$$Z = ((COS(A) - COS(A+B) \times 1.5)) - (((COS(22.5-A) - (COS 22.5)) \times 2.78))$$

The A & B variables are the top and bottom encoder offset values from the mastered positions, as disclosed above. This converted Y & Z data along with the raw X axis data is all that is needed to generate a full mathematical picture of the screw pattern. Once the screw pattern is known, the next function is to mathematically draw lines between these 3D points in space. This will generate a wire pattern where all bends appear at the screw centers, which is not desirable. The bends in the wire need to be someplace between the screws, and straight sections still have to pass through the screw centers.

In one embodiment, the goal on the bent was ⅓ on the distance between the starting screw and its neighbor. This ⅓ ratio provides a strong and tight (width) pattern over the screws. Regardless of the number of screws in the procedure, a straight line is drawn between screws 2 & 3 and beyond by about ½ the screw's distance. At this point the focus is on the bend between screws 1 & 2. It is desired to have the bend to fall on the 2-3 line extension, and it should be at ⅔ ratio point on the vector line coming from screw #1. If a circle was drawn with screw #2 as its center, and with a radius of ⅓ the straight line distance between screws 1 & 2, it will intersect the 2-3 extension very close to the desired bend point. The true bend point will be formed at the intersection of the 2-3 extension and at a radius from screw #2 equal to: (⅓ the straight line distance between screws 1 & 2/COS of the angle formed by the intersection of the 2-3 line, the 1-2 line). This angle is referred to as "A3". Once these angles are calculated, all line lengths and angles can be calculated for the balance of the rod form.

Figure 8:
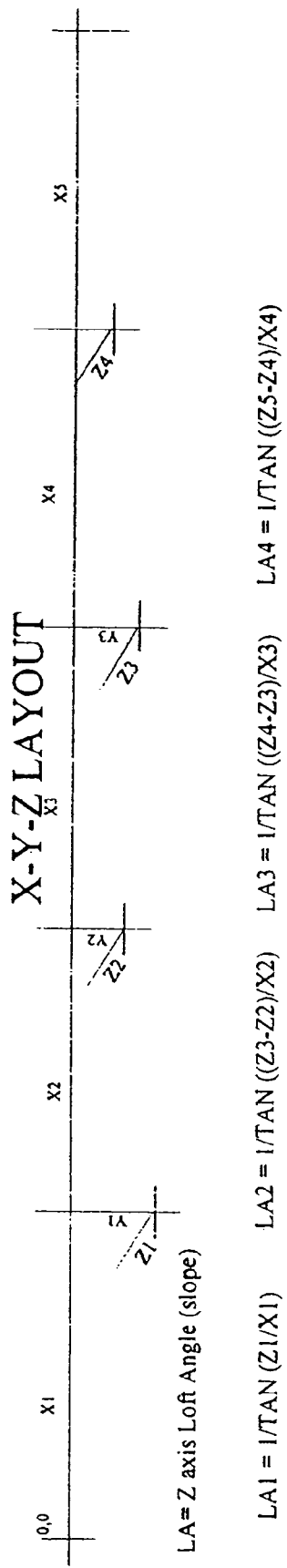

FIGS. 7 and 8 graphically illustrate a typical calculation sheet for a five level procedure. Angle A3 is equal to A1+A2 as shown in FIGS. 7 and 8. A typical spreadsheet showing the results of these calculations is as follows:

| X1 | X2 | X3 | X4 | X5 | X6 |
|---|---|---|---|---|---|
| 0 | 1.39 | 2.786 | 4.207 | 5.584 | 6.974 |
| Ang 1 | Ang 2 | Ang 3 | B | L1 = L2 | Ang 4 |
| 0.2649 15.175 | 0.1067 6.1109 | 0.3715 21.286 | 1.4402 | 0.7728 | 137.43 |
| Ang 8 | D | Ang 9 | Ang 10 | L6 = L7 | Ang 11 |
| 0.115 6.5867 | 1.3861 | 0.243 13.921 | 0.3579 20.508 | 0.714 | 138.98 |
| Mov X1 | Bend 1 | Mov X2 | Rot 180 | Bend 2 | Mov X3 |
| 1.2728 | 42.571 | 2.9 | 180 | 20.032 | 1.4372 |
| X count | Z count | X count | Y count | Z count | X count |
| 403956 | 178052 | 371198 | 6400 | 113431 | 183964 |
| Y1 | Y2 | Y3 | Y4 | Y5 | Y6 |
| 0 | −0.377 | −0.227 | −0.324 | −0.165 | 0 |
| L3 | Ang5 | Ang6 | C | L4 = L5 | Ang 7 |
| 1.404 | 0.0682 3.9051 | 0.1748 10.016 | 1.4243 | 0.7232 | 159.97 |
| Ang 12 | E | Ang 13 | L8 = L9 | Ang 14 | |
| 0.1176 6.7406 | 1.3511 | 0.243 13.921 | 0.696 | 152.16 | |
| Rot 180 | Bend 3 | Mov X4 | Rot 180 | Bend 4 | Mov X5 |
| 180 | 41.015 | 1.4101 | 180 | 27.842 | 1.196 |
| Y count | Z count | X count | Y count | Z count | X count |
| 6400 | 173591 | 180487 | 6400 | 135823 | 153089 |

The above spreadsheet example only deals with the X & Y-axis. The Z-axis offset may be vectorially added later. The Z-axis offset will have negligible effect on the bend angles or bend positions. At the time the actual bend is made, this Z vector may be combined with the bend calculations, and it will be entered as a rotary variable of the rod position, not the angular included angle of the bend itself.

Rows 2 & 3 on the above spreadsheet contain the X & Y variables. The X variables come into these cells directly from the Excel macro. The Y variables are calculated from rotary data placed into cells by the same macro. The equation to do this calculation is as follows:

$$Y=(SIN(A) \times 2.78)+(SIN(A+B) \times 1.5)$$

The majority of the functionality of the spreadsheet relates to the calculation and display angles and lengths to duplicate the manual process illustrated in FIGS. 7 and 8. The bottom row of this spreadsheet displays the actual servo variables that are sent to the mechanical bending system. The units expressed are actual encoder counts of the servomotors of the bending system station. Further detail of these variables and ratios are disclosed below.

Figure 9:
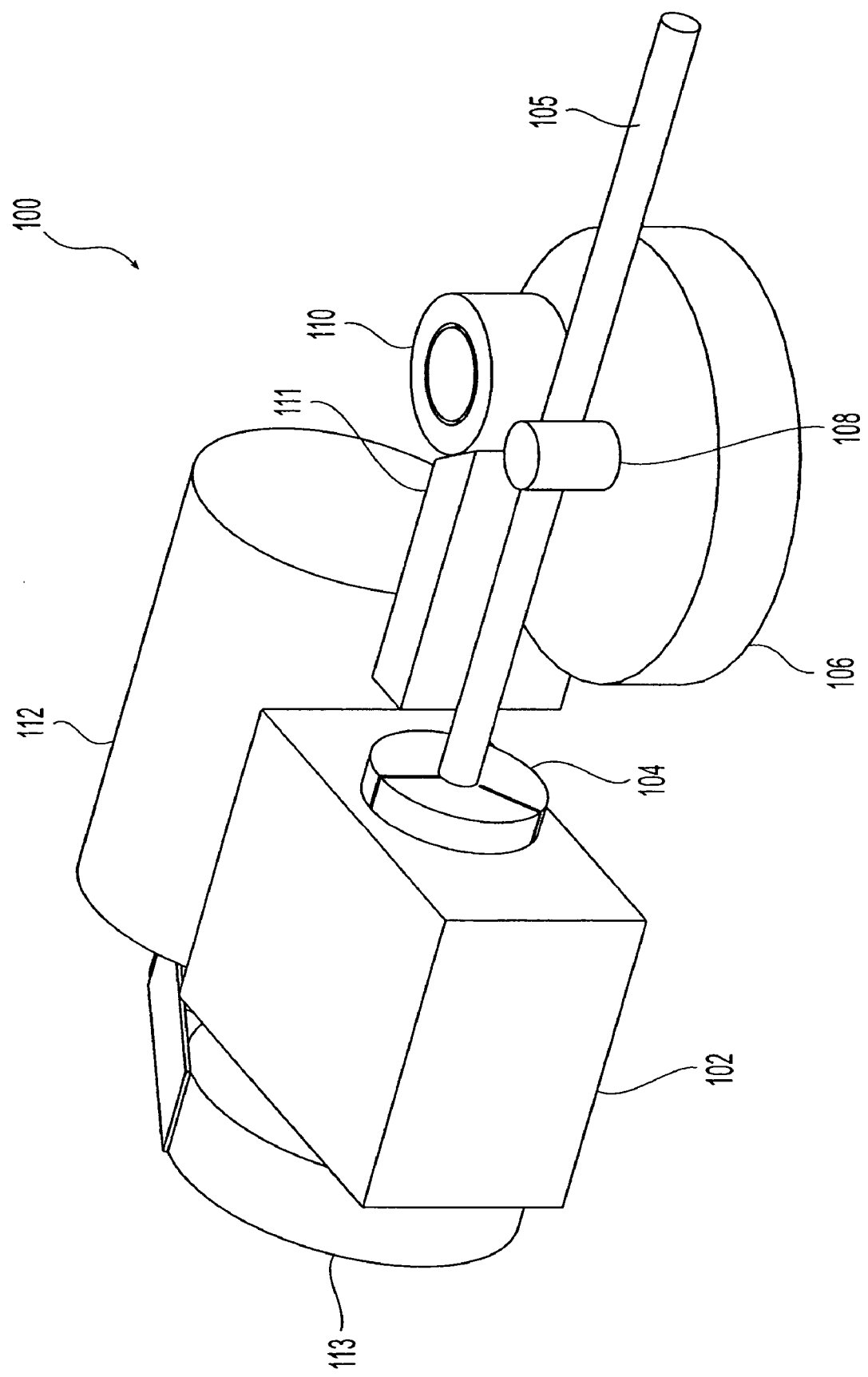
FIG. 9 is a perspective view of a bending system in accordance with one embodiment of the present invention.

FIG. 9 is a perspective view of a bending system 100 in accordance with one embodiment of the present invention. Bending system 100 uses three electric servomotors to handle the axial feed of the rod, which is the X-axis, the vertical deflection of the rod, which is the Y-axis, and lateral deflection of the rod, which is the Z-axis.

As shown in FIG. 9, bending system 100 includes a headstock or spindle assembly 102, which contains a collet 104 which grips the rod 105. Rod 105 passes along a stationary rectangular block 111, which handles the reaction forces of the bending operation. Bending system 100 further includes a vertical axis disk 106, which contains a center cam follower 108, and an orbiting cam follower 110. This whole disk assemble rotates to form the bend. One of the servomotors 112 drives a horizontal rotary spindle 113, and thus rotates rod 105. This is accomplished through a timing belt and pulley system, which has a reduction ratio of 3.2:1. This is the Y-axis of the system.

Figure 10:
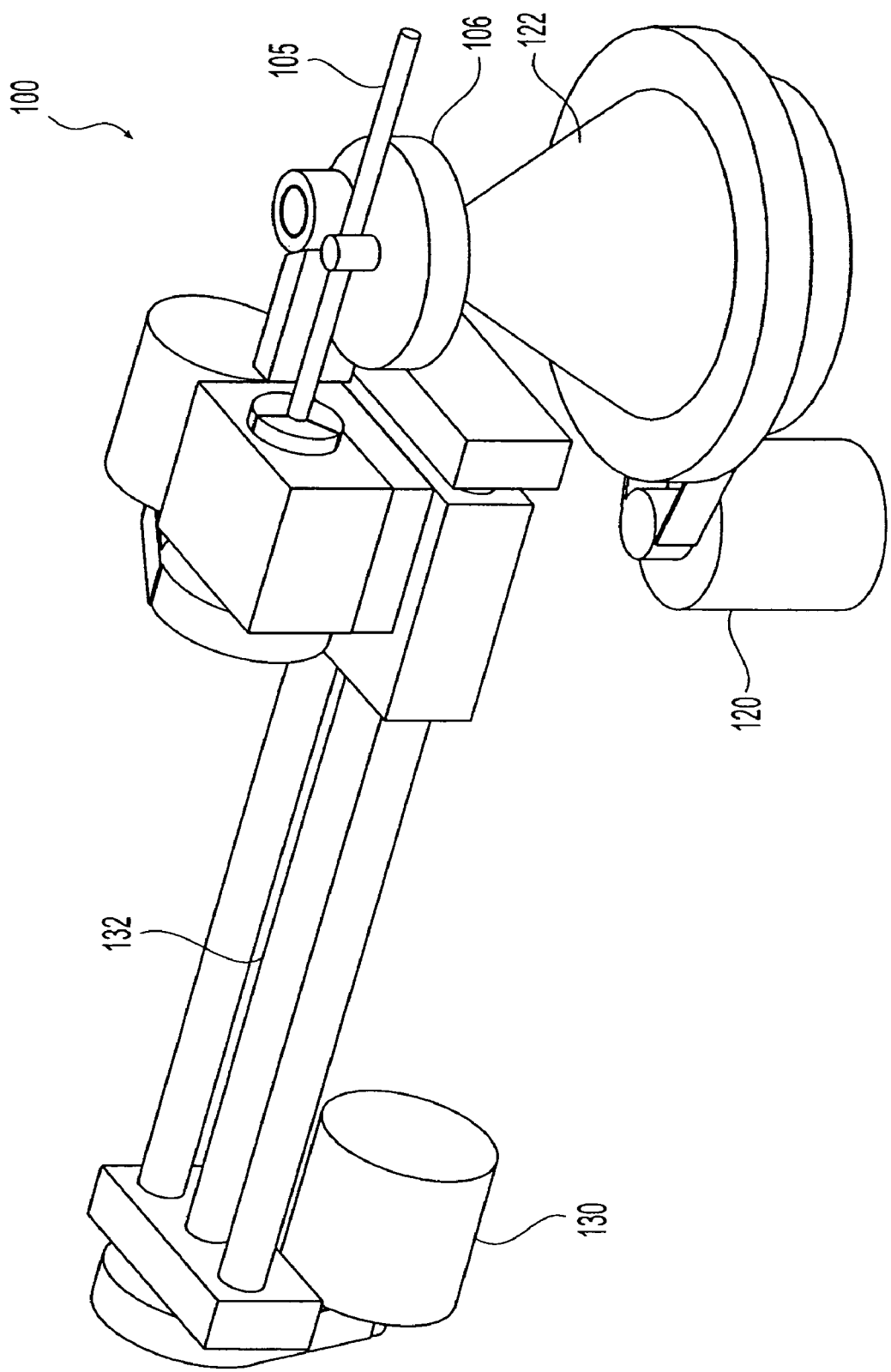
FIG. 10 is an additional perspective view of the bending system in accordance with one embodiment of the present invention.

FIG. 10 is an additional perspective view of the bending system 100 in accordance with one embodiment of the present invention. A second servomotor 120 drives the vertical axis rotation, which moves disk 106 and bends rod 105. This is also accomplished through a timing belt and pulley system, which has a reduction ratio of 6:1. In addition to the belt reduction, this axis also uses a gear reducer 122, which has a reduction of 43:1. This provides a total reduction or torque increase of 258. The second servomotor 120, pulley system and disk 106 forms the Z-axis of bending system 100.

A third servomotor 130 is used to drive a screw on a linear slide. This is the X-axis of the system, and it is also a timing belt reduction and has a ratio of 3.2:1. The center horizontal cylinder 132 of the slide is the screw, and it has a screw pitch of 0.1" (10 threads per inch). Therefore one turn of the motor shaft will move the slide load (the rotating spindle) 1/32".

All three of the servomotors are identical in one embodiment and have an encoder resolution of 4000 counts per revolution. These individual encoder counts are used in the commanded moves of each axis. These counts are calculated in Excel, as shown in the above spreadsheet. The below table summarizes the motion per encoder counts for each axis:

| Axis | Total Reduction | Motion/Encoder Count |
|---|---|---|
| X (linear) | 32:1 | 1/(4000 × 32) = .0000078 Inches |
| Y (rotary) | 3.2:1 | 1/((4000 × 3.2)/360) = .028 Degree |
| Z (rotary) | 258:1 | 1/((4000 × 258)/360) = .00035 Deg. |

FIG. 11 is an additional perspective view of the bending system 100 in accordance with one embodiment of the present invention. In FIG. 11, the X-axis is retracted into the home position. Also shown in FIG. 11 is a photoelectric or fiber optic sensor 138 which crosses through stationary rectangular block 111. Sensor 138 is mounted normal to rod 105 and in one embodiment is an inline pair of small diameter cylinders, with an air gap for rod 105 to pass through. Sensor 138 sees the leading edge of the rod as it moves along with the X-axis slide.

In operation, in one embodiment system 100 initially has all servo axes sent to a home or known position. A new rod is placed and clamped into the collet. The correct servo program is downloaded into the servo controller from the computer system. A start button or a keystroke initiates the bend cycle. The X-axis servo moves the X-axis slide away from home towards spindle assembly 102. It moves at a rapid traverse rate until the photoelectric or fiber optic sensor sees the rod end. At this point it stops and the position counters are set to zero. The X-axis slide continues to move towards the bending station for a preprogrammed distance. This distance is equal to the distance from the photoelectric/fiber optic sensor to the centerline of the bend rollers plus another fixed distance which will be the distance from the rod end to the first bend.

The X motion is then stopped and the Z motion is initiated to achieve the desired first bend. The bending station is then sent back to its home position, and the X motion is initiated to the center of the next bend. Prior to making the next bend, some type of Y motion will be initiated to place the rod rotation angle in the correct quadrant. If the desired rod was to be a flat "S" or flat zigzag and be able to lay flat on a table, and thus have no elevation change, the Y motion would be zero degrees or 180 degrees. Likely it will not be flat and therefore some positive or negative elevation must be introduced. The Y motion handles this elevation change before making the next bend.

The desired number, degree, and axial position of the bends is continued until the rod shaping is complete. At this point the machine operator is prompted to remove the rod from the collet. To accomplish removal, the collet is manually loosened and the rod is slid out of the machine in a direction away from the spindle. As soon as the rod is clear of the photoelectric/fiber optic sensor, the machine automatically homes itself, and makes itself ready for the next part.

Figure 13:
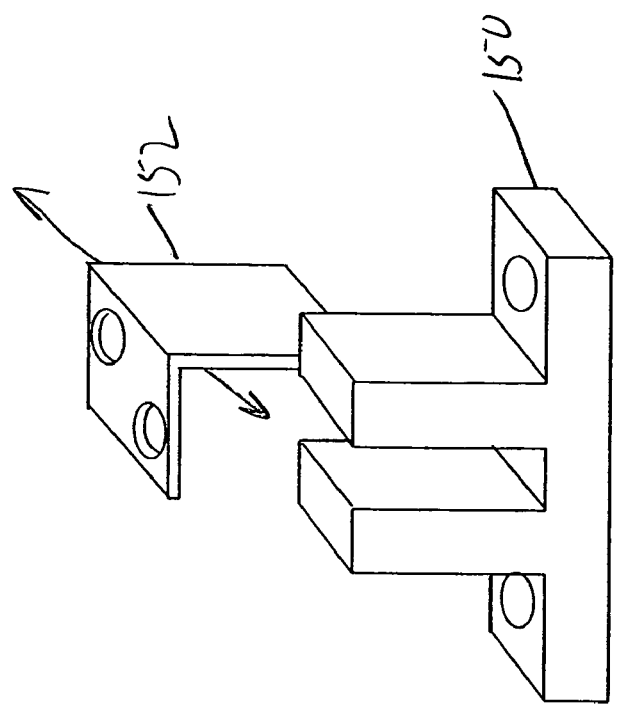
FIGS. 12 and 13 are perspective views of stationary sensors in accordance with one embodiment of the present invention.
Figure 12:
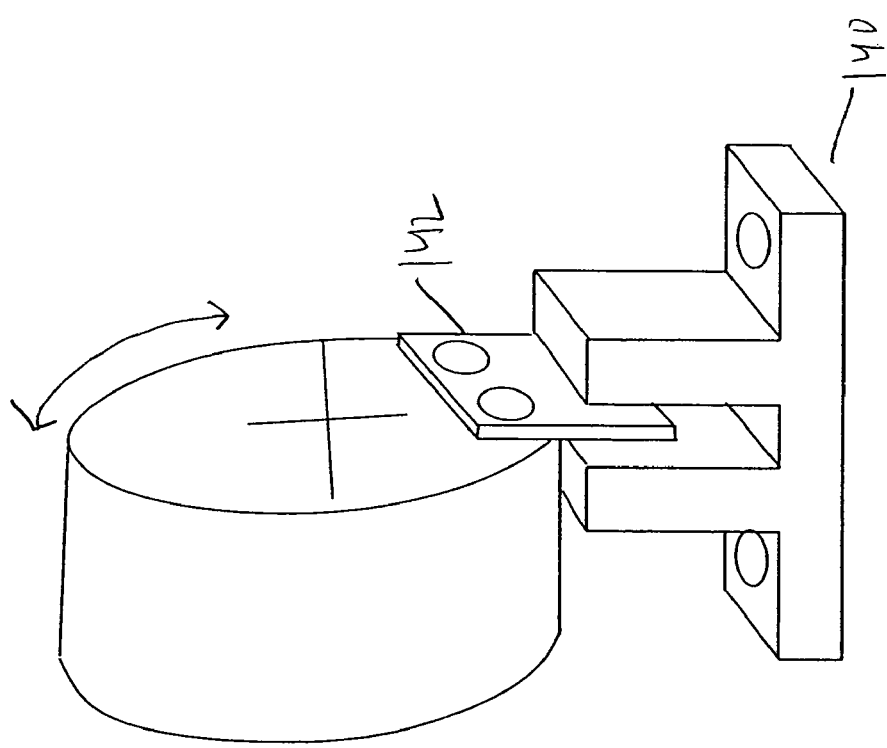

FIGS. 12 and 13 are perspective views of stationary sensors 140 and 150 in accordance with one embodiment of the present invention. Each servo axis of the bending system is equipped with photoelectric through beam sensors for over travel (sensor 150, one at each end), and a photoelectric through beam sensor for the home switch (sensor 140). The moving part of each axis contains a metal flag (flags 142 and 152) or interrupter for these switches. The servo amplifier provides TTL Level I/O lines to handle the reading of these switches as well as other push button switches used in the bending operation. The outputs of this I/O section provides light indicators or audible beepers to alert the machine operator if necessary.

Figure 14:
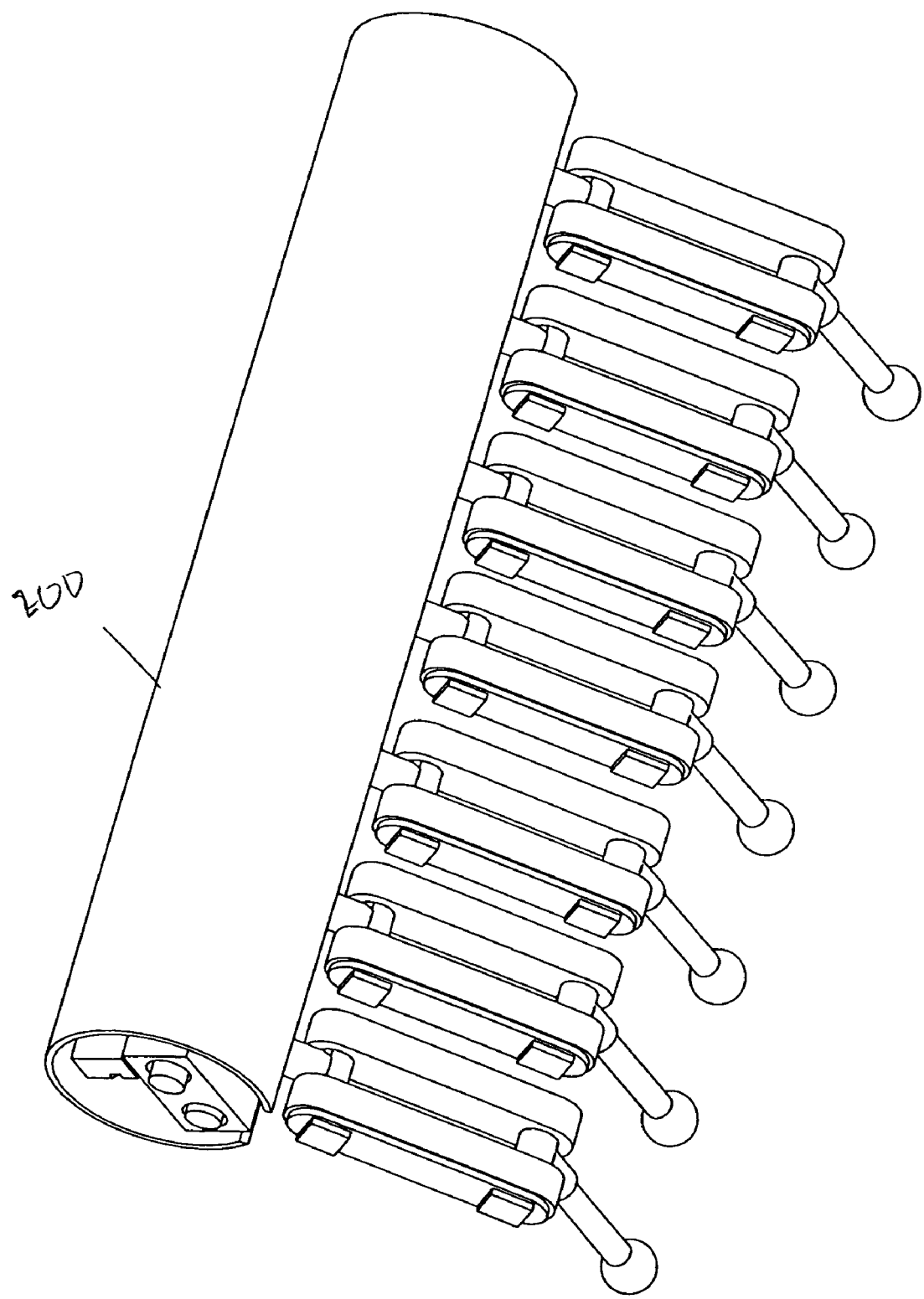
FIG. 14 is a perspective view of a six level sensor assembly that is placed in a tube in accordance with one embodiment of the present invention.

FIG. 14 is a perspective view of a six level sensor assembly that is placed in a tube 200 in accordance with one embodiment of the present invention. Not shown are end caps, which will protect the internal electronics as well as support the two internal bearing rods, and thus allow each sensor to float axially within tube 200. Tube 200 also acts as the supporting handle for the surgeon. Tube 200 can be grasped in both hands with the thumbs on the bottom and palms wrapped around to the top. The fingers will rest over the top and make contact with each sensor linkage. Pressure will be applied and felt for each linkage.

In one embodiment, the outside diameter tube 200 is approximately 1½", and as disclosed above the finger linkages will each be 1½" long. The power and communication cable for the tube assembly will exit through one of the end caps.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. An automated screw rod bender comprising:
    a sensing system for sensing a first position of each of a plurality of screws that are inserted into a vertebrae;
    a computing system for converting the first positions into geometric coordinates of the screws and generating a corresponding plurality of rod bending parameters; and
    a rod bending system for bending a rod based on the rod bending parameters,
    said sensing system comprising a plurality of sensing arms, each of said sensing arms comprising:
        a sensor measurement ball configured to fit into a socket of one of said screws;
        a first shaft coupled to said measurement ball;
        a first rotary sensor configured to measure first coordinates of said first shaft;
        a second shaft coupled to said first shaft;
        a second rotary sensor configured to measure second coordinates of said second shaft;
        a sensor block coupled to said second shaft and slidably mounted on at least one linear shaft; and
        a linear sensor configured to measure a second position of said sensor block on said shaft.

2. The rod bender of claim 1, wherein the geometric coordinates comprise an X-axis coordinate, a Y-axis coordinate and a Z-axis coordinate of each of the screws.

3. The rod bender of claim 1, said rod bending system comprising:
    a headstock for gripping the rod;
    a first servomotor coupled to said headstock for rotating the rod;
    a vertical axis disk; and
    a second servomotor coupled to said vertical axis disk for moving said vertical axis disk and bending the rod.

4. The rod bender of claim 3, said rod bending system further comprising:
    a center cam follower coupled to said vertical axis disk; and
    an orbital cam follower coupled to said vertical axis disk.

5. The rod bender of claim 3, said rod bending system further comprising:
    a linear slide coupled to said headstock; and
    a third servomotor for moving said headstock along said linear slide.

6. The rod bender of claim 1, said computing system comprising:
    a memory; and
    a processor coupled to said memory;
    wherein said memory stores instructions that, when executed by said processor, cause said processor to calculate said rod bending parameters using a spreadsheet.

* * * * *